United States Patent [19]

Shah

[11] 4,224,310
[45] Sep. 23, 1980

[54] DENTIFRICE COMPOSITIONS

[75] Inventor: Nutan B. Shah, New Rochelle, N.Y.

[73] Assignee: Richardson-Merrell, Inc., Wilton, Conn.

[21] Appl. No.: 72,173

[22] Filed: Sep. 4, 1979

[51] Int. Cl.$^2$ .......................... A61K 7/22; A61K 7/16
[52] U.S. Cl. ........................................ 424/54; 424/49
[58] Field of Search ...................................... 424/49–58

[56] References Cited

U.S. PATENT DOCUMENTS

| | | | |
|---|---|---|---|
| 3,699,221 | 10/1972 | Schole et al. | 424/49 |
| 3,988,434 | 10/1976 | Schole et al. | 424/49 |

*Primary Examiner*—Shep K. Rose
*Attorney, Agent, or Firm*—Eugene O. Retter; George W. Rauchfuss, Jr.

[57] ABSTRACT

Dentifrice composition having strontium disodium ethylenediamine tetraacetate formed in situ.

2 Claims, No Drawings

DENTIFRICE COMPOSITIONS

FIELD OF THE INVENTION

This invention related to dentifrice compositions containing strontium disodium ethylenediamine tetracetate and to a process of preparing said compositions by the formulation of strontium disodium ethylenediamine tetraacetate in situ and obtaining a product with an unacceptable salty or metallic taste.

BACKGROUND OF THE INVENTION

It has heretofore been known to improve oral hygiene by applying to teeth certain dentifrice compositions containing strontium disodium ethylinediamine tetraacetate such as for example as disclosed in U.S. Pat. Nos. 3,699,221 and 3,988,434. In said patents it is disclosed that the strontium disodium ethylenediamine tetraacetate can be formed in situ but in each instance said product is formed by the use of strontium chloride as the reactant. However, while the desired reaction product is obtained the reaction also leads to the formation of by-products that leave the resulting dentifrice composition unacceptably salty and metallic tasting.

BRIEF DESCRIPTION OF THE INVENTION

It has now been discovered according to the present invention that such dentifrice compositions wherein strontium disodium ethylenediamine tetraacetate is formed in situ can be formed by a method of in situ synthesis such that the problem of saltiness or metallic tastiness in the resulting product is avoided and a more stable product is obtained. This is accomplished according to the present invention by forming strontium disodium ethylenediamine tetraacetate in situ by the reaction of disodium ethylenediamine tetraacetate with strontium carbonate in water and in the absence of any strontium chloride. The solution formed in this reaction can then be formulated into any suitable dentifrice preparation according to known procedures, such as for example, according to the disclosures in previously mentioned U.S. Pat. Nos. 3,699,221 and 3,988,434.

DETAILED DESCRIPTION OF THE INVENTION

Dentifrice compositions of this invention are formulated using strontium disodium ethylenediamine tetraacetate formed in situ in water by the reaction of disodium ethylenediamine tetraacetate with strontium carbonate in the absence of strontium chloride. The reaction proceeds according to the following reaction scheme:

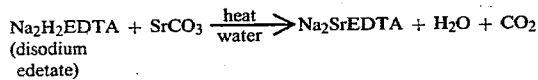

$$Na_2H_2EDTA + SrCO_3 \xrightarrow[water]{heat} Na_2SrEDTA + H_2O + CO_2$$
(disodium edetate)

The disodium edetate is dissolved in hot water of about 70°–80° C. and strontium carbonate is added in small quantities with stirring to form the desired product. The pH at the beginning of the reaction is around pH 5 and shifts to pH 7 to 8 when the reaction is completed.

Exemplary of the formation of the desired products is the following reaction. About 4800 g of water is heated to 70° C. and 816 g of disodium acetate is dissolved in the heated water. Thereafter 322 g of strontium carbonate are slowly added to the solution. The reaction is complete when the effervescent action has stopped and a pH of about 7 is reached.

When the reaction is completed the solution can be formulated into suitable dentifrice products such as toothpastes, mouthwashes, lozenges, gums, powders, troches and the like. As examples of formulations made with the in situ formed strontium disodium ethylenediamine tetraacetate of this invention there may be mentioned the following exemplary water containing dentifrice formulations.

| FORMULATION A Toothpaste | |
|---|---|
| Ingredients | % w/w |
| Disodium edetate | 8.82 |
| Strontium Carbonate | 3.50 |
| Sorbitol Solution | 12.00 |
| Glycerine | 9.00 |
| Sodium carboxymethylcellulose | 1.30 |
| Hydroxyethylcellulose | 0.50 |
| Strontium Carbonate | 30.00 |
| Cetyl pyridinium chloride | 0.10 |
| Sodium Saccharin | 0.20 |
| Silicon dioxide | 1.80 |
| Flavor | 0.75 |
| Leaf alcohol | 0.001 |
| Methylparaben | 0.06 |
| Propylparaben | 0.02 |
| Polyethylene glycol-20-sorbitan isostearate | 0.70 |
| Sodium lauryl sulfate | 1.00 |
| Hydrochloric acid | 1.20 |
| Water | q.s. |

| FORMULATION B Toothpaste | |
|---|---|
| Ingredients | % w/w |
| Disodium edetate | 8.82 |
| Strontium Carbonate | 3.50 |
| Sorbitol Solution | 12.00 |
| Glycerine | 9.00 |
| Sodium carboxymethylcellulose | 1.30 |
| Hydroxyethylcellulose | 0.50 |
| Strontium Phosphate | 30.00 |
| Cetylpyridinium chloride | 0.10 |
| Sodium Saccharin | 0.20 |
| Silicon dioxide | 1.80 |
| Flavor | 0.75 |
| Leaf alcohol | 0.001 |
| Methylparaben | 0.06 |
| Propylparaben | 0.02 |
| Polyethylene glycol-20-sorbitan isostearate | 0.70 |
| Sodium laurylsulfate | 1.00 |
| Hydrochloric acid | 0.27 |
| Water | q.s. |

| FORMULATION C | |
|---|---|
| Ingredients | % w/w |
| Disodium edetate | 8.82 |
| Strontium Carbonate | 3.50 |
| Sorbitol Solution | 12.00 |
| Glycerine | 9.00 |
| Sodium carboxymethylcellulose | 1.30 |
| Hydroxyethylcellulose | 0.50 |
| Insoluble sodium metaphosphate | 30.00 |
| Cetyl pyridinium chloride | 0.1 |
| Sodium Saccharin | 0.2 |
| Silicon dioxide | 1.8 |
| Methylparaben | 0.06 |
| Propylparaben | 0.02 |
| Sodium laurylsulfate | 1.00 |
| Hydrochloric acid | 0.1 |

| FORMULATION C | |
|---|---|
| Ingredients | % w/w |
| Flavor | 0.75 |
| Leaf alcohol | 0.001 |
| Polyethylene glycol-20-sorbitan isostearate | 0.50 |
| Water | q.s. |

| FORMULATION D Toothpaste | |
|---|---|
| Ingredients | % w/w |
| Disodium edetate | 8.82 |
| Strotium Carbonate | 3.50 |
| Sorbitol Solution | 12.0 |
| Glycerine | 9.0 |
| Sodium carboxymethylcellulose | 1.3 |
| Aluminum hydroxide-Hydral C331 | 30.0 |
| Cetyl pyridinium chloride | 0.1 |
| Sodium Saccharin | 0.2 |
| Silicon dioxide | 1.8 |
| Methylparaben | 0.06 |
| Propylparaben | 0.02 |
| Sodium lauryl sulfate | 1.00 |
| Flavor | 0.75 |
| Leaf alcohol | 0.001 |
| Sodium ricinoleate | 2.0 |
| Water | q.s. |

| FORMULATION E Mouthwash | |
|---|---|
| Ingredients | % w/w |
| Disodium edetate | 8.82 |
| Strontium Carbonate | 3.50 |
| Sorbitol Solution | 10.00 |
| Glycerine | 5.00 |
| Pluronic F-127 - polyoxyalkylene derivitive of propylene glycol | 0.75 |
| Sodium Saccharin | 0.10 |
| Menthol, Natural | 0.13 |
| Peppermint Oil | 0.10 |
| Sodium riconoleate | 0.50 |
| Sodium chloride | 0.58 |
| FD&C Blue #1 | 0.03 |
| Water | q.s. |

I claim:

1. In a dentifrice formulation having incorporated therein strontium disodium ethylenediamine tetraacetate formed in situ the improvement comprising forming the strontium disodium ethylenediamine tetraacetate in situ by the reaction of disodium ethylenediamine tetraacetate with strontium carbonate in water and in the absence of any strontium chloride.

2. A dentifrice formulation of claim 1 wherein the reaction takes place in the presence of water heated to about 70° to 80° C.